United States Patent
Doubler et al.

(10) Patent No.: US 7,105,029 B2
(45) Date of Patent: Sep. 12, 2006

(54) SKELETAL FIXATION DEVICE WITH LINEAR CONNECTION

(75) Inventors: Robert L. Doubler, Ida, MI (US); John E. Hammill, Sr., Rossford, OH (US)

(73) Assignee: Zimmer Spine, Inc., Minneapolis, MN (US)

( * ) Notice: Subject to any disclaimer, the term of this patent is extended or adjusted under 35 U.S.C. 154(b) by 191 days.

(21) Appl. No.: 10/358,427

(22) Filed: Feb. 4, 2003

(65) Prior Publication Data

US 2003/0149487 A1 Aug. 7, 2003

Related U.S. Application Data

(60) Provisional application No. 60/354,408, filed on Feb. 4, 2002.

(51) Int. Cl.
*A61F 2/32* (2006.01)
*A61B 17/70* (2006.01)

(52) U.S. Cl. ..................... 623/22.42; 606/61

(58) Field of Classification Search ............ 623/22.42, 623/22.19, 22.2, 22.29; 606/59, 61, 69, 71, 606/72, 73, 99, 100, 104, 151; 411/39, 40, 411/41, 42, 259, 267, 268, 361, 385, 431, 411/435; 433/173

See application file for complete search history.

(56) References Cited

U.S. PATENT DOCUMENTS

| 255,428 | A |   | 3/1882 | Graham |
|---|---|---|---|---|
| 351,474 | A | * | 10/1886 | Stevens ............ 411/432 |
| 590,294 | A |   | 9/1897 | Archer |
| 3,797,336 | A | * | 3/1974 | Howe ............ 81/125 |
| 4,378,187 | A |   | 3/1983 | Fullerton |
| 4,419,026 | A |   | 12/1983 | Leto |
| 4,618,300 | A | * | 10/1986 | Goebel ............ 411/433 |
| 4,653,969 | A |   | 3/1987 | Summerlin et al. |
| 4,684,284 | A |   | 8/1987 | Bradley, Jr. |
| 4,822,223 | A |   | 4/1989 | Williams |
| 4,836,196 | A |   | 6/1989 | Park et al. |
| 4,854,304 | A |   | 8/1989 | Zielke |
| 4,887,595 | A |   | 12/1989 | Heinig et al. |
| 4,887,596 | A |   | 12/1989 | Sherman |
| 4,946,458 | A |   | 8/1990 | Harms et al. |
| 4,974,888 | A | * | 12/1990 | Childers ............ 292/251 |
| 5,002,542 | A |   | 3/1991 | Frigg |
| 5,110,244 | A |   | 5/1992 | Garman |
| 5,129,900 | A |   | 7/1992 | Asher et al. |
| 5,133,717 | A |   | 7/1992 | Chopin |
| 5,324,150 | A |   | 6/1994 | Fullerton |
| 5,427,488 | A |   | 6/1995 | Fullerton et al. |
| 5,487,744 | A |   | 1/1996 | Howland |
| 5,549,608 | A |   | 8/1996 | Errico et al. |
| 5,569,247 | A |   | 10/1996 | Morrison |
| 5,591,166 | A |   | 1/1997 | Bernhardt et al. |
| 5,613,816 | A |   | 3/1997 | Cabahug |
| 5,613,968 | A |   | 3/1997 | Lin |
| 5,628,740 | A |   | 5/1997 | Mullane |

(Continued)

FOREIGN PATENT DOCUMENTS

DE 197 20 782 A 1 11/1998

(Continued)

*Primary Examiner*—Eduardo C. Robert
*Assistant Examiner*—David Comstock
(74) *Attorney, Agent, or Firm*—Wood, Herron & Evans, LLP

(57) ABSTRACT

A modular bone implant is connected together using linear compression rather than torque.

11 Claims, 4 Drawing Sheets

U.S. PATENT DOCUMENTS

| | | | |
|---|---|---|---|
| 5,653,765 A | 8/1997 | McTighe et al. |
| 5,716,357 A | 2/1998 | Rogozinski |
| 5,749,690 A | 5/1998 | Kutz |
| 5,788,443 A | 8/1998 | Cabahug |
| 5,800,108 A | 9/1998 | Cabahug |
| 5,800,435 A | 9/1998 | Errico et al. |
| 5,816,761 A | 10/1998 | Cassatt et al. |
| 6,050,997 A | 4/2000 | Mullane |
| 6,063,090 A | 5/2000 | Schlapfer |
| 6,090,111 A | 7/2000 | Nichols |
| 6,102,952 A | 8/2000 | Koshino |
| 6,162,234 A | 12/2000 | Freedland et al. |
| 6,179,512 B1 | 1/2001 | Gibson et al. |
| RE37,227 E | 6/2001 | Brodbeck |
| 6,254,602 B1 | 7/2001 | Justis |
| 6,537,005 B1 | 3/2003 | Denham |
| 6,602,255 B1 | 8/2003 | Campbell et al. |
| 6,623,485 B1 | 9/2003 | Doubler et al. |
| 2002/0114680 A1 | 8/2002 | Stoewer |
| 2003/0073996 A1 | 4/2003 | Doubler et al. |
| 2003/0149487 A1 | 8/2003 | Doubler et al. |
| 2004/0006342 A1 | 1/2004 | Altarac et al. |

FOREIGN PATENT DOCUMENTS

| | | |
|---|---|---|
| DE | 100 05 386 A 1 | 8/2001 |
| WO | WO 00/15125 | 3/2000 |

* cited by examiner

SKELETAL FIXATION DEVICE WITH LINEAR CONNECTION

RELATED APPLICATIONS

This application claims the benefit of the filing date of Provisional Application No. 60/354,408 filed Feb. 4, 2002.

FIELD OF THE INVENTION

This invention relates to bone implants and methods of connecting components together without placing torque forces on the skeleton. The invention may be used in surgical appliances, including dentistry, which have an element temporarily or permanently fixed in the bone and supporting another element acting as a prosthesis or brace.

BACKGROUND OF THE INVENTION

In the field of orthopedic surgery there are various procedures requiring insertion of an anchor, pin, peg, screw or cage into the bones of the skeleton to correct anatomical defects. Other procedures include reconstruction, such as artificial joints and teeth. All of these procedures, requiring fixations of an appliance in the bone are currently performed using threaded connections between the components.

For example, in hip replacements using modular joints, the artificial head of the hip joint is screwed on the end of a pin fixed in the femur. Torque applied to the head of the joint will normally be translated to the pin. In many spinal corrections, pedicle screws are placed in the vertebrae to support cages or plates for fixing spatial orientation. The connection of the screws to the ancillary devices usually put torque on the vertebrae through the pedicle screw. Similarly, in placing artificial teeth on pegs inserted in the jaw bone, torque may be applied through the fitting of the teeth.

DESCRIPTION OF THE PRIOR ART

U.S. Pat. No. 5,487,744 issued Jan. 30, 1996 to Howland discloses a spinal fixation device using several pedicle screws to anchor several rods extending along the spine to maintain spatial orientation. The pedicle screws and the rods are connected by screws and/or nuts requiring torque which may be translated to the spine.

Brodbeck, U.S. Pat. No. RE 37,227, issued Jun. 12, 2001, discloses an artificial tooth screwed onto a threaded anchor in the jaw. Torque on the tooth could translate to the anchor.

U.S. Pat. No. 5,653,765, issued Aug. 5, 1997 to McTighe et al discloses a modular hip prosthesis wherein the ball is connected to the pin in the femur by a threaded bolt. Tightening the upper elements to fix the orientation could put torque forces on the femur pin.

What is needed in the art is a non-torqued connection for the components of modular implants.

SUMMARY OF THE INVENTION

Accordingly, it is an objective of the instant invention to teach a method of connecting components of a bone implant using linear compression.

It is a further objective of the instant invention to teach the use of a modular implant having an element anchored in the bone and a support element for ancillary devices, each with a cooperating coupling component adapted to be secured together without torque forces.

It is yet another objective of the instant invention to teach a linear coupling for medical implants with a pressure limiting element.

It is a still further objective of the invention to teach an instrument for use with the modular implants to apply linear compression for securing the components of the implant.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

Figure 1:
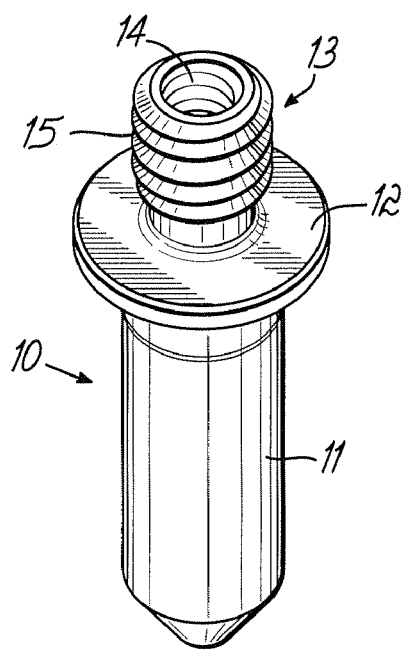
FIG. 1 shows a perspective of a bone implant component of this invention.
Figure 2:
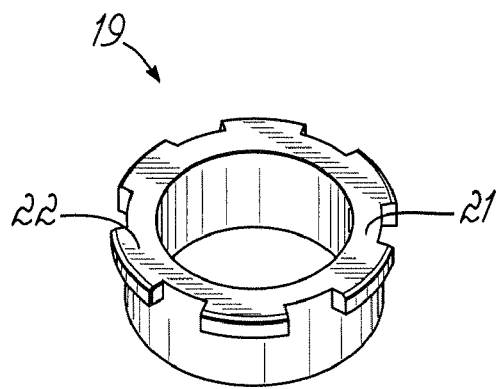
FIG. 2 shows a perspective of a compression ring of this invention.
Figure 3:
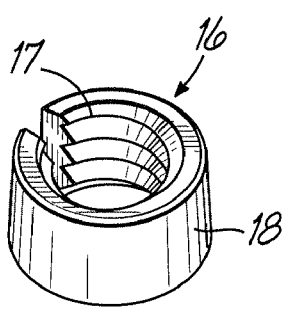
FIG. 3 shows a perspective of a split ring of this invention.
Figure 4:
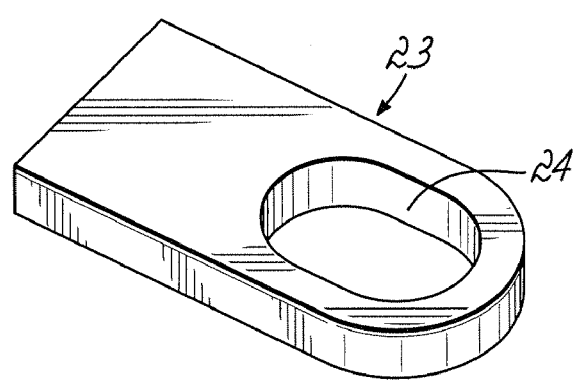
FIG. 4 shows a perspective of a connector of general utility for use with the implant of this invention.

The bone implant 10, shown in FIG. 1, is a representation of an implant of general utility having a bone contacting element 11, a collar 12 and a hollow shank 13 with interior threads 14 and exterior threads 15. The split ring 16, shown in FIG. 3, is loosely threaded over the external threads 15 engaging threads 17. The external surface 18 of split ring 16 is tapered or conical in form. The compression ring 19, shown in FIG. 2, has a tapered interior surface 20 which is complementary to the taper of split ring 16. The compression ring 19 has a flange 21 about the upper surface. The flange 21 has lugs 22 formed in a C-shape for engaging an extractor (not shown) used to remove, or disconnect the coupling. The connector 23, shown in FIG. 4, represents any ancillary apparatus which would be held in place by the implant 10. In this instance, the connector 23 has an aperture 24 that accommodates shank 13 and secures the connector to the implant. The connector 23 rests on collar 12. For example, the connector could be a component of a set of spinal rods.

Figure 5:
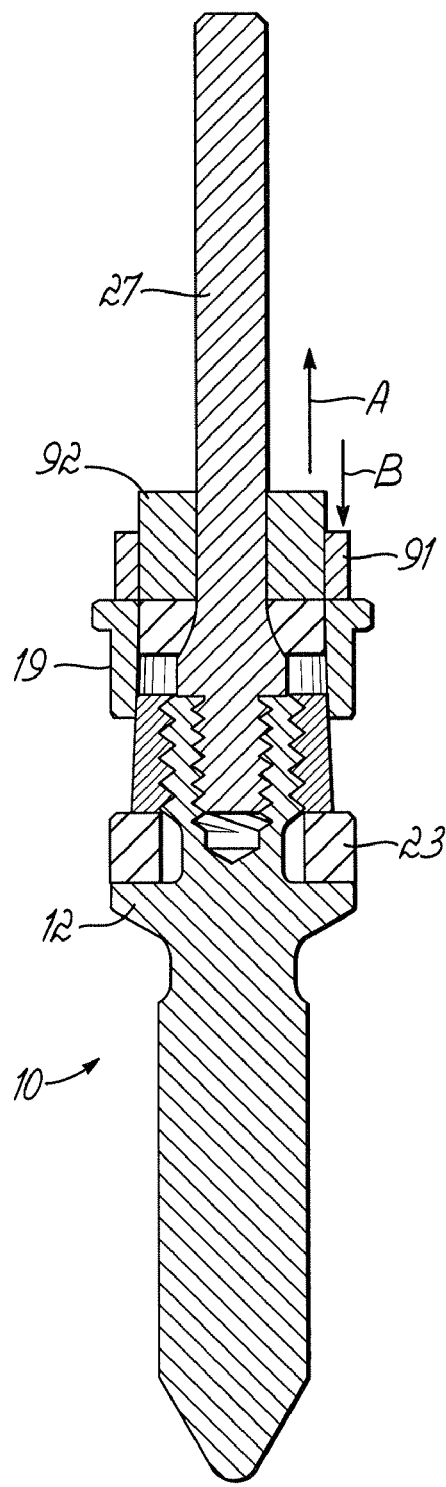
FIG. 5 shows a side view partly in section of the implant initial assembly of this invention.
Figure 6:
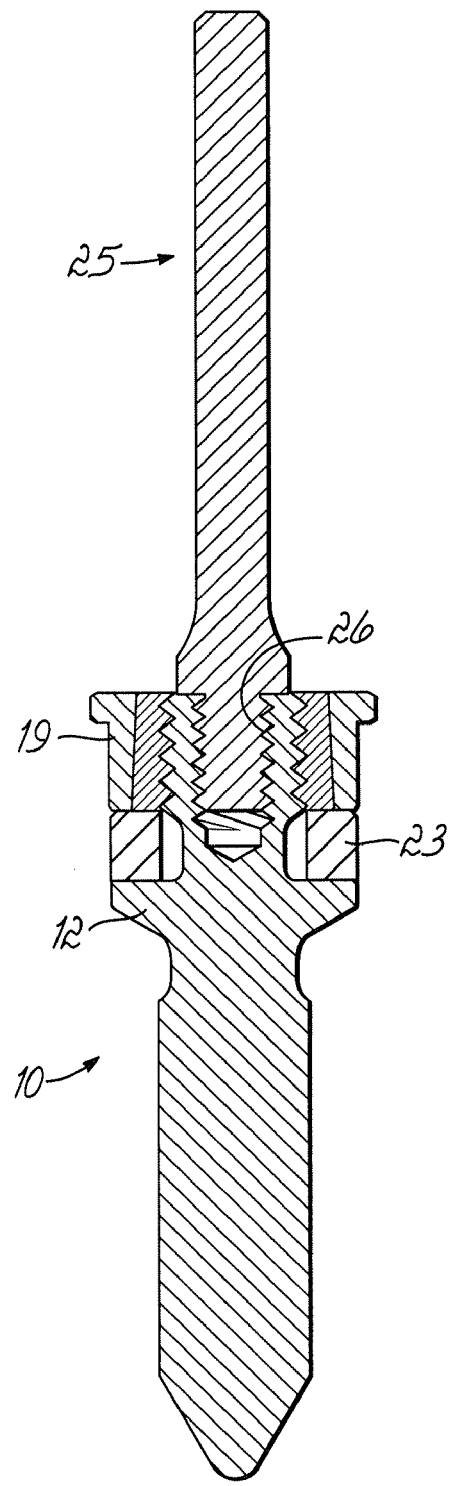
FIG. 6 shows a side view partly in section of the implant final assembly of this invention.

FIGS. 5 and 6 show the assembly of the bone implant 10. In FIG. 5 the bone implant has been associated with the connector 23 of an ancillary device. The split ring 16 has been loosely threaded on the exterior threads 15 of the shank with the external taper extending from a large diameter in contact with the connector 23 to a smaller diameter. The tapered wall of compression ring 19 is frictionally engaged with the tapered wall of the split ring. A compression rod 25 has been threaded into the internal threads of the shank. Compression rod 25 has external threads 26 and an elongated extension 27. External threads 26 engage internal threads 14 of the implant. In FIG. 6, the final assembly is shown. The linear compression coupling results from equal and opposite forces, A and B, shown in FIG. 5, being applied to the compression ring and the split ring, simultaneously. The linear force applied to the split ring 16 is applied through compression rod 25. As the instrument 90 applies progressive pressure through concentric pistons 91 and 92, the compression ring 19 moves downwardly reducing the diameter of the split ring through the interaction of the complementary tapers. The interior threads of the split ring tightly engage the external threads of the shank. Because of the configuration of these threads the split ring threads are ramped upwardly on the external threads of the shank.

Once all slack is taken out of the linear coupling, the extension rod can break at the limit of optimum pressure. Alternatively, the instrument 90 may have a gauge for setting the desired pressure.

Figure 7:
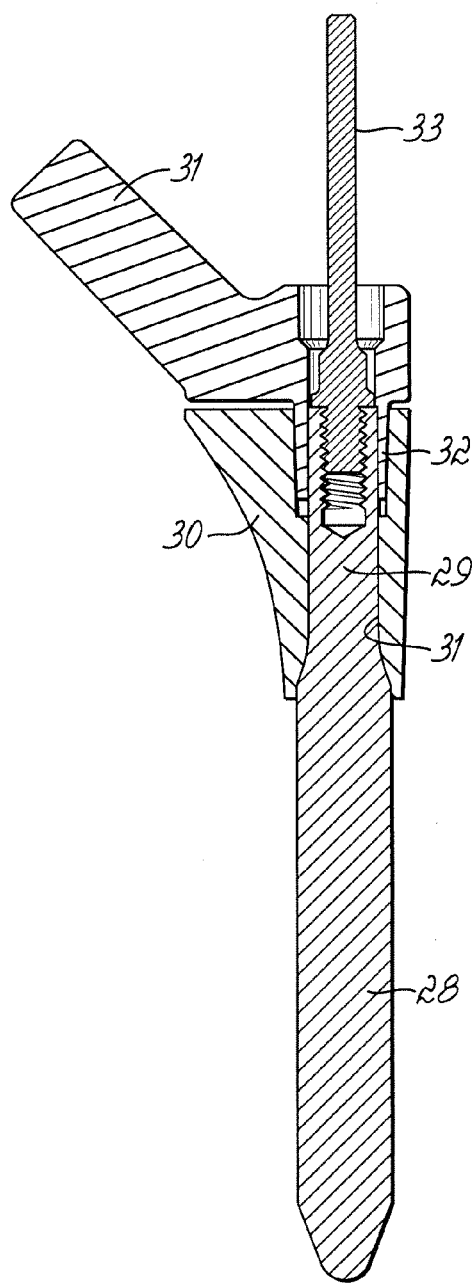
FIG. 7 shows an artificial hip preliminary assembly with linear coupling of this invention.
Figure 8:
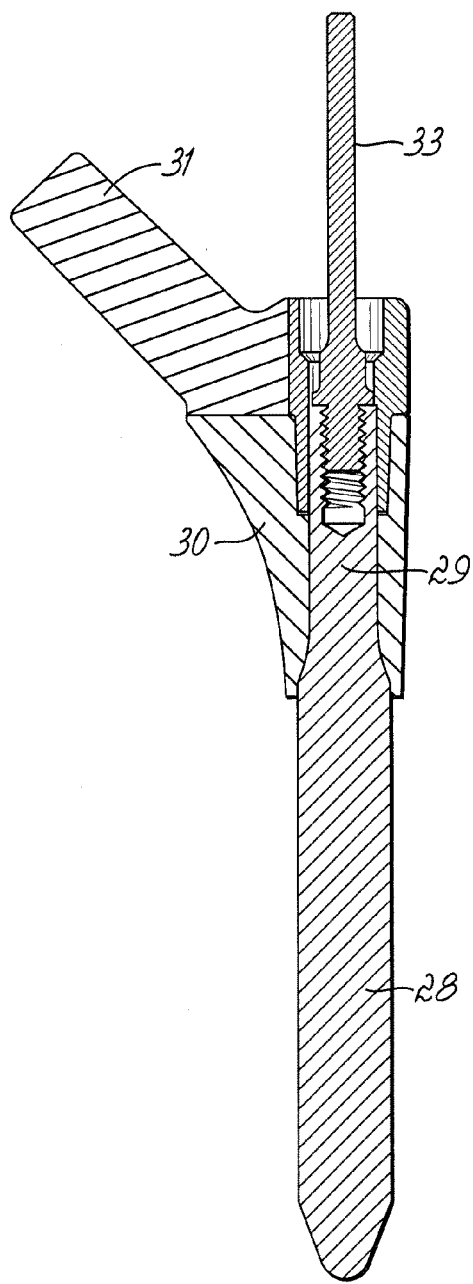
FIG. 8 shows the artificial hip of FIG. 7 final assembly.

In FIGS. 7 and 8, the linear coupling is shown applied to the modular element of an artificial hip joint. The pin 28 is implanted in the femur and has a tapered upper end 29. The collar 30 has a complementary taper 31 with the upper end 29 of the pin. The arm 31 which is connected to the artificial ball joint (not shown)has an extension with a taper 32 on the exterior surface. The upper end of the pin has internal threads for connecting with a compression rod 33. An instrument 90, as shown in FIG. 5, is applied to the piston rod 33 and the upper surface of the arm 31. Linear compression is applied through the instrument 90 and the tapered surfaces of the modules of the hip joint move into locked position without exerting torque on the pin or femur.

Figure 9:
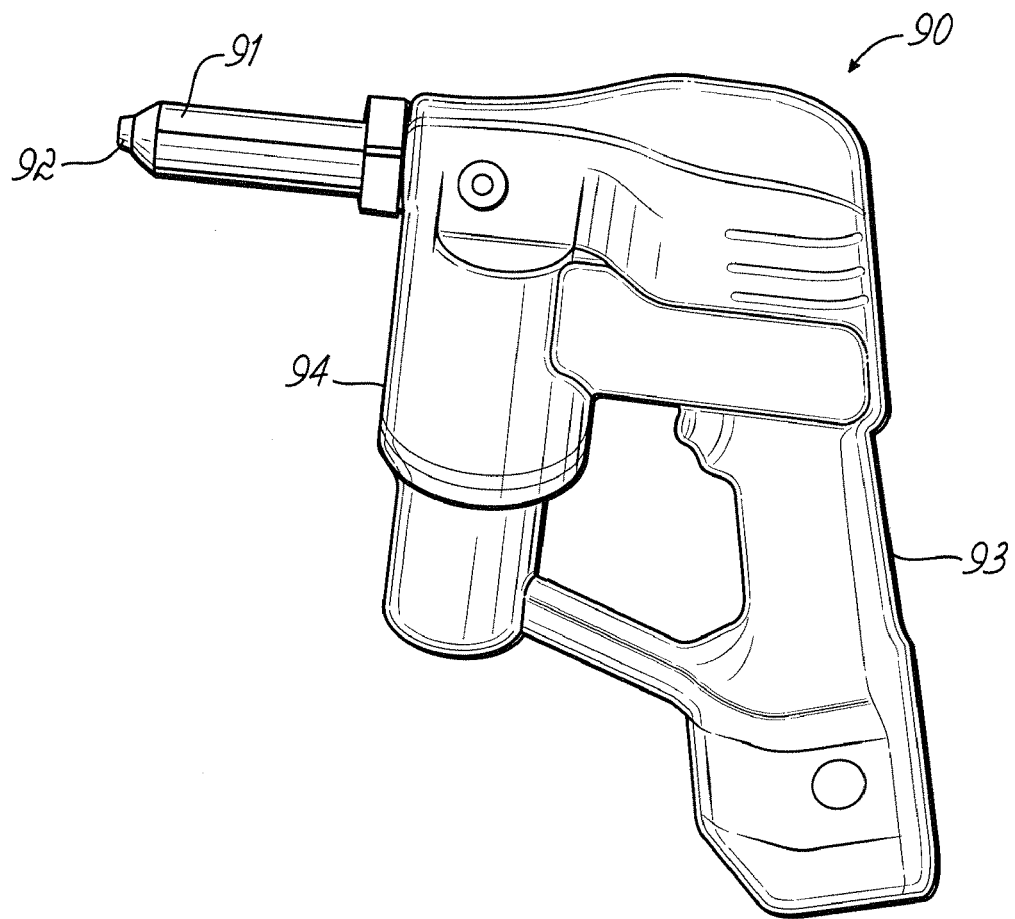
FIG. 9 shows an implement for applying linear compression.

FIG. 9 shows an instrument having a pistol grip 93, a power source 94 and concentric pistons 91 and 92. Piston 92 is sized to grip the compression rod. Piston 91 is sized to seat on the compression ring.

In the event that an implant must be removed, a similar instrument may be employed. One of the pistons would have a flange with flat lugs. The instrument would be placed over the implant and turned a quarter turn to engage the flat lugs with the C-shaped lugs and opposite force is applied. The linear coupling is separated without placing pressure on the implant.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

We claim:

1. A modular implant for supporting a prosthesis comprising an anchor element adapted to be attached to a skeletal bone and a support element adapted for connection with an ancillary device, said anchor element and said support element having cooperating coupling components for linear engagement whereby engaging said cooperating coupling components of said anchor element and said support element form a secure connection which transmits no force to the skeletal bone, wherein said anchor element has one end portion for attachment to a bone and another end portion supporting a shank, said shank having at least one tapered surface, said support element including a portion having a complementary tapered surface, said tapered surface and said complementary tapered surface comprise said cooperating coupling components whereby linear force along said cooperating coupling components ramps said tapered surface and said complementary tapered surface together forming a secure connection transmitting no torque to said anchor element, wherein said shank has a circumferential tapered surface and said support element has a ring with an internal complementary tapered surface, said ring adapted to fit over said shank with said internal tapered surface engaging said circumferential tapered surface whereby said linear force displaces said internal complementary tapered surface and said circumferential tapered surface into fixed intimate contact.

2. A modular implant of claim 1 wherein said support element has a first position and a second position, a compression ring surrounds said support element and is adapted to move said support element from said first position to said second position in response to said linear force.

3. A modular implant of claim 1 wherein an ancillary device is adjustably mounted on said shank intermediate said one end portion and said support element whereby said anchor element and said support element fix said ancillary device in a desired position by said secure connection.

4. A modular implant of claim 3 wherein said shank has a central cavity, said central cavity formed with an internal connector, said at least one tapered surface on the exterior of said central cavity, an elongated compression rod with a connector on one end to mate with said internal connector in said shank and a second end adapted to engage a compression instrument, said support element has a ring with an internal complementary tapered surface, said ring adapted to fit over said shank with said internal tapered surface engaging said external tapered surface, a compression ring surrounds said support element and is adapted to move said support element from said first position to said second position in response to said linear force.

5. A modular implant of claim 4 wherein said support element ring is a split ring with internal tapered surfaces, said compression ring adapted to reduce the diameter of said split ring to form said secure connection.

6. A modular implant of claim 4 wherein said compression instrument is adapted to apply a calibrated amount of linear pressure.

7. A modular implant of claim 6 wherein said compression rod is adapted to separate from said connector upon application of said calibrated amount of linear pressure.

8. A modular implant for supporting a prosthesis comprising an anchor element adapted to be attached to a skeletal bone and a support element adapted for connection with an ancillary device, said anchor element and said support element having cooperating coupling components for linear engagement whereby engaging said cooperating coupling components of said anchor element and said support element form a secure connection which transmits no force to the skeletal bone, wherein said anchor element has one end portion for attachment to a bone and another end portion supporting a shank, said shank having at least one tapered surface, said support element including a portion having a complementary tapered surface, said tapered surface and said complementary tapered surface comprise said cooperating coupling components whereby linear force along said cooperating coupling components ramps said tapered surface and said complementary tapered surface together forming a secure connection transmitting no torque to said anchor element, wherein an ancillary device is adjustably mounted on said shank intermediate said one end portion and said support element whereby said anchor element and said support element fix said ancillary device in a desired position by said secure connection, wherein said shank has a central cavity, said central cavity formed with an internal connector, said at least one tapered surface on the exterior of said central cavity, an elongated compression rod with a connector on one end to mate with said internal connector in said shank and a second end adapted to engage a compression instrument, said support element has a ring with an internal complementary tapered surface, said ring adapted to fit over said shank with said internal tapered surface engaging said external tapered surface, a compression ring surrounds said support element and is adapted to move said support element from said first position to said second position in response to said linear force.

9. A modular implant of claim 8 wherein said support element ring is a split ring with internal tapered surfaces, said compression ring adapted to reduce the diameter of said split ring to form said secure connection.

10. A modular implant of claim 8 wherein said compression instrument is adapted to apply a calibrated amount of linear pressure.

11. A modular implant of claim 10 wherein said compression rod is adapted to separate from said connector upon application of said calibrated amount of linear pressure.

* * * * *